United States Patent
Dierker

(10) Patent No.: US 9,012,514 B2
(45) Date of Patent: Apr. 21, 2015

(54) EMOLLIENTS AND COSMETIC COMPOSITIONS BASED ON SPECIFIC BRANCHED HYDROCARBONS

(75) Inventor: Markus Dierker, Duesseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 505 days.

(21) Appl. No.: 11/817,385

(22) PCT Filed: Feb. 23, 2006

(86) PCT No.: PCT/EP2006/001641
§ 371 (c)(1),
(2), (4) Date: Aug. 29, 2007

(87) PCT Pub. No.: WO2006/094642
PCT Pub. Date: Sep. 14, 2006

(65) Prior Publication Data
US 2008/0161418 A1    Jul. 3, 2008

(30) Foreign Application Priority Data

Mar. 4, 2005   (DE) .......................... 10 2005 009 853
Mar. 11, 2005  (DE) .......................... 10 2005 011 691

(51) Int. Cl.
| A61K 8/31 | (2006.01) |
| A61K 31/01 | (2006.01) |
| A61K 9/107 | (2006.01) |
| A61Q 19/00 | (2006.01) |
| C25B 3/02 | (2006.01) |
| C25B 3/10 | (2006.01) |

(52) U.S. Cl.
CPC . *A61K 8/31* (2013.01); *A61Q 19/00* (2013.01); *C25B 3/02* (2013.01); *C25B 3/10* (2013.01)

(58) Field of Classification Search
None
See application file for complete search history.

(56) References Cited

U.S. PATENT DOCUMENTS

| 2,680,713 | A |  | 6/1954 | Lindsey et al. |
| 2,760,926 | A |  | 8/1956 | Kronenthal |
| 3,818,105 | A | * | 6/1974 | Coopersmith et al. ......... 514/789 |
| 3,992,268 | A | * | 11/1976 | Antos ............................ 205/462 |
| 4,853,217 | A |  | 8/1989 | Francke et al. |
| 5,169,626 | A | * | 12/1992 | Tanner et al. .................... 424/66 |
| 5,607,972 | A | * | 3/1997 | Motley .......................... 514/558 |
| 5,627,056 | A | * | 5/1997 | Casey et al. ................... 435/134 |

(Continued)

FOREIGN PATENT DOCUMENTS

| DE | 103 17 781 | 11/2004 |
| DE | 103 24 508 | 12/2004 |

(Continued)

OTHER PUBLICATIONS

"On the Synthesis of Branched Fatty Acids" Lipids, vol. 28 (10) pp. 889-897 (1993, Gronowitz et al).*

(Continued)

*Primary Examiner* — Ileana Popa
*Assistant Examiner* — Nicole Babson
(74) *Attorney, Agent, or Firm* — Servilla Whitney LLC

(57) ABSTRACT

A cosmetic or pharmaceutical composition is provided. The composition contains a mixture of oils prepared by Kolbe electrolysis of branched chain fatty acids and mixtures of branched chain fatty acids with straight chain fatty acids. The fatty acids containing from 3 to 26 carbon atoms. The oils are a mixture of oils with different spreading rates (spreading cascade).

6 Claims, 1 Drawing Sheet

Spreading values for various hydrocarbons

(56) References Cited

U.S. PATENT DOCUMENTS

| | | | |
|---|---|---|---|
| 5,627,057 A * | 5/1997 | Singh et al. | 435/135 |
| 5,759,969 A * | 6/1998 | Tsaur et al. | 510/158 |
| 5,763,497 A * | 6/1998 | Ikeda et al. | 424/401 |
| 5,882,663 A * | 3/1999 | Koeniger et al. | 514/762 |
| 6,007,800 A * | 12/1999 | Dubief et al. | 424/70.1 |
| RE38,441 E * | 2/2004 | Jacks et al. | 424/64 |
| 2005/0079986 A1* | 4/2005 | Mitchell et al. | 510/285 |
| 2007/0081959 A1 | 4/2007 | Schmid et al. | |

FOREIGN PATENT DOCUMENTS

| | | |
|---|---|---|
| EP | 1 512 392 | 3/2005 |
| JP | 61 147890 | 7/1986 |

OTHER PUBLICATIONS

Identification of 5,9-dimethylheptadecane as a sex pheromone of the moth *Leucoptera scilla*, Naturwissenschaften, vol. 74 (1987) Francke et al, pp. 143-144.*

Hans-Jurgen Schäfer. "Recent Contributions of Kolbe Electrolysis to Organic Synthesis". Electrochemistry IV Topics in Current Chemistry. vol. 152, 1990, pp. 91-151.*

Kolbe, "Untersuchungen ueber die Elektrolyse organischer Vergindungen", Liebigs Ann. Chem., vol. 69, 1849, pp. 257-294.

Barry et al.,"Reactions of Anodically Generated Radicals with Oxygen," Journ. of American Chem. Soc., vol. 98, 1976, pp. 8098-8101.

\* cited by examiner

Spreading values for various hydrocarbons
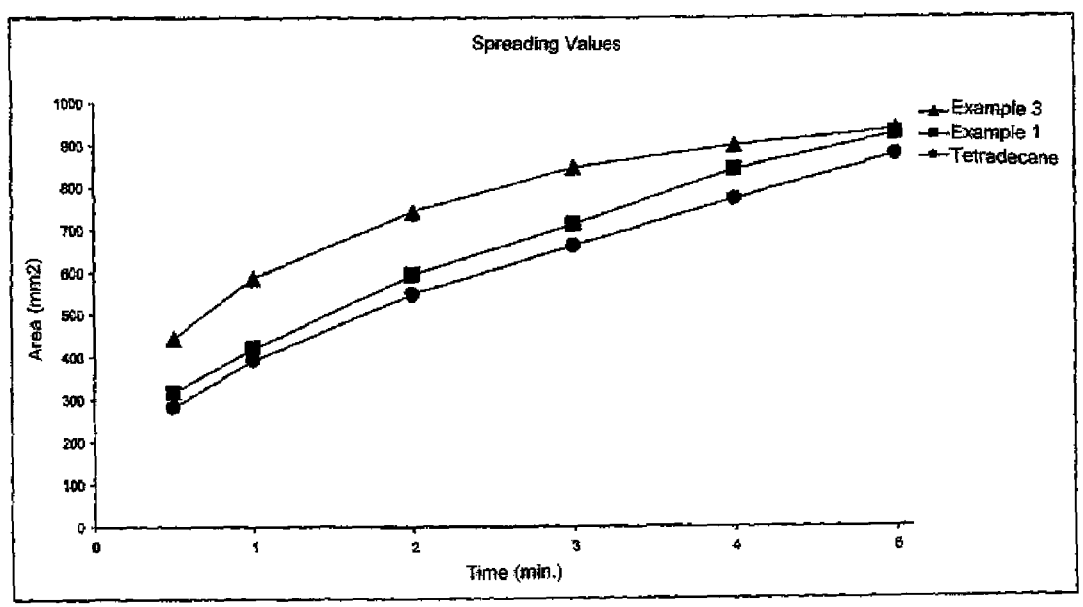

EMOLLIENTS AND COSMETIC COMPOSITIONS BASED ON SPECIFIC BRANCHED HYDROCARBONS

RELATED APPLICATIONS

This application is filed under 35 U.S.C. §371, claiming priority from PCT/EP2006/001641 filed Feb. 23, 2006, which claims priority from DE 10 2005 009 853.3 filed Mar. 4, 2005, and DE 10 2005 011 691.4 filed Mar. 11, 2005; the entire contents of each application are incorporated herein by reference.

FIELD OF THE INVENTION

The invention relates to cosmetic compositions with oil components on a hydrocarbon basis obtained using Kolbe synthesis and to the use of these hydrocarbons.

BACKGROUND OF THE INVENTION

In the area of cosmetic emulsions for skin and hair care, a great number of requirements are specified by the consumer. Apart from the cleaning and grooming effects which determine the intended application, value is placed on such diverse parameters as the best possible dermatological compatibility, good refatting properties, polished appearance, optimal sensory perception and long shelf life.

Preparations which are used for the cleaning and care of the human skin and hair generally contain, in addition to a series of surface active substances, primarily oil components and water. Hydrocarbons, ester oil components as well as vegetable and animal oils/fats/waxes are used as oil components/emollients. To meet high market demands concerning sensory properties and optimal, dermatological compatibility, new oil components and emulsifying agent mixtures are continuously being developed and tested.

The application of hydrocarbons in cosmetic compositions has been long established. Take, for example, mineral oil components and liquid paraffin used as inert oil components. These have the disadvantage from a sensory standpoint that they leave behind a "heavy" feeling on the skin and spread poorly. It is known to use product mixtures of the most varied hydrocarbons with improved spreading ability, as are obtainable in accordance with the methods described in DE 103 17 781 or DE 103 24 508. Such mixtures are difficult to characterize and contain a great number of different single components, whose individual contributions to the spreading ability can only be ascertained with great difficulty.

The object of the present invention was accordingly to provide alternative, easily spreadable, volatile hydrocarbons for use in cosmetics, these hydrocarbons being easily produced with high yields. A further aspect was to produce hydrocarbons that are suitable as a silicone substitute, in order to demonstrate the sensory profile of volatile silicones.

BRIEF DESCRIPTION OF THE INVENTION

It has surprisingly been found that hydrocarbons produced using Kolbe electrolysis of fatty acids are suitable for use as volatile emollients with good spreading qualities in cosmetics, and are specifically obtained in elevated yield. Kolbe electrolysis itself has long been established as the chosen method for the production of hydrocarbons (H. Kolbe, *Liebigs Ann. Chem.* 1849, 69, 257-294) and as such constitutes the prior art. The resulting hydrocarbons which may purposefully be produced are of a symmetrical structure but have not hitherto been described for use in cosmetics.

BRIEF DESCRIPTION OF THE DRAWINGS

The FIGURE is a graph of hydrocarbons spreading versus time for the hydrocarbons of Examples 1 and 3 and tetradecane.

DETAILED DESCRIPTION OF THE INVENTION

The present invention accordingly provides cosmetic compositions containing at least one hydrocarbon with at least 10 carbon atoms, which hydrocarbon is obtained by Kolbe electrolysis of (a) of at least one branched $C_6$-$C_{26}$ fatty acid or (b) a mixture of at least one linear $C_3$-$C_{26}$ fatty acid and at least one branched $C_4$-$C_{26}$ fatty acid. According to the invention, the hydrocarbon must have a chain length of at least 10 carbon atoms in order to be suitable for cosmetic applications. Accordingly, if a linear $C_3$ fatty acid (propionic acid) is reacted with a branched fatty acid, the branched fatty acid must contain at least 9 carbon atoms so that the resulting hydrocarbon comprises a total of at least 10 carbon atoms. Conversely, when a branched $C_4$ fatty acid is used, the linear fatty acid must comprise at least 8 carbon atoms. For the purposes of the invention, the cosmetic or pharmaceutical composition can contain both a single hydrocarbon which has been obtained by Kolbe electrolysis, as well as a product mixture that arises by Kolbe electrolysis of different branched $C_6$-$C_{26}$ fatty acids or by Kolbe electrolysis of linear $C_3$-$C_{26}$ fatty acids and branched $C_4$-$C_{26}$ fatty acids. The advantageous solution for each individual case will depend on the particular intended application.

The advantage of Kolbe electrolysis is that it does not lead to the isomerization of the radicals. The metal cations move under the influence of direct current towards the cathode, while the negatively charged carboxylates move towards the anode where, by means of anodic oxidization, decarboxylation starts. The arising alkyl radicals then undergo dimerization. The products obtained by dimerization are symmetrical and have structures which exactly reproduce, i.e. retain, the structural characteristics of the fatty acids. The emollients obtained by Kolbe electrolysis thus display a substitution pattern which cannot be produced through other preparative methods (for example oligomerization). This distinguishes the alkanes obtained by Kolbe electrolysis from already known, branched alkane emollients. Accordingly, Kolbe electrolysis of, 2-ethylhexane for example, specifically gives rise to diethyldecane which is of a symmetrical structure (J. E. Barry, M. Finkelstein, E. A. Mayeda, S. D. Ross, J. of American Chem. Soc. 1976, 98, 8098-8101).

Scheme 1

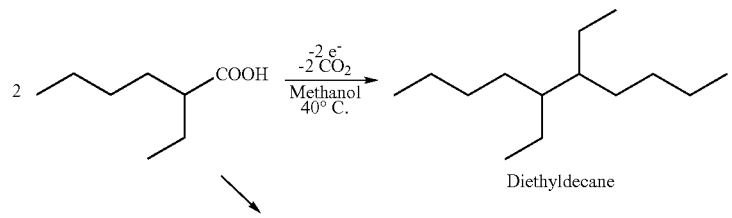

Diethyldecane

-continued

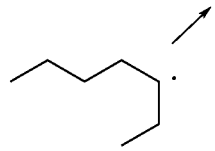

Depending on whether a single fatty acid or a fatty acid mixture is used as the starting material, the number of products to be expected can be controlled precisely. When carboxylic acid mixtures are electrolyzed, all possible products of symmetrical and asymmetrical radical combinations are obtained. In contrast to hydrocarbon mixtures which are produced by condensation reactions and polymerizations, the composition of the product mixture is more readily controllable, exactly defined and far less complex when produced by Kolbe electrolysis. In this way, branching points can also be purposefully inserted resulting in hydrocarbons and hydrocarbon mixtures developed with optimized spreading cascades, the use of which in cosmetics leads to sensory advantages. According to the invention, a mixture of pivalic acid and isostearic acid in a 1:1 molar ratio can be subjected to Kolbe electrolysis and the reaction product incorporated into cosmetic formulations. The use of $C_6$-$C_{22}$ fatty acids for Kolbe electrolysis is preferred according to the invention as the resulting hydrocarbons exhibit better properties for cosmetic applications.

Compositions which are particularly preferred according to the invention are those which are characterized in that the hydrocarbon produced by Kolbe electrolysis has at most 22 carbon atoms. Hydrocarbons with a maximum of 22 carbon atoms are distinguished by better volatility and sensory advantages in the final formulations and are especially suitable as a silicone substitute.

In a further preferred embodiment according to the invention, the compositions contain at least one hydrocarbon, produced by electrolysis of ethylhexanoic acid, isononanoic acid, isodecanoic acid, isostearic acid, monomer fatty acid, neodecanoic acid or any desired mixture of these fatty acids, or a mixture of the previously mentioned fatty acid(s) with pivalic acid or cyclohexanecarboxylic acid.

Monomer fatty acid is a term familiar to a person skilled in the art for mixtures of branched, unsaturated fatty acids. According to the invention, it is additionally suitable to use Cekanoic C8 (isooctanoic acid), Cekanoic C9 (isononanoic acid: 3,5,5, trimethylhexanoic acid and 2,5,5-trimethylhexanoic acid) and Cekanoic C10 (isodecanoic acid), which are isomeric mixtures, from Exxon Mobil.

In a further preferred embodiment, the compositions contain at least one saturated hydrocarbon which has been formed by Kolbe electrolysis. The use of saturated hydrocarbons is preferred, as they are less susceptible to oxidation.

The compositions according to the invention preferably contain the hydrocarbons produced by Kolbe electrolysis in a quantity of 0.1-50 wt. % relative to the total composition.

It can be advantageous to use branched fatty acids which do not exhibit any branching in the alpha position. Branching in alpha position can sometimes lead to poorer yields during Kolbe electrolysis.

The present invention also provides the use of hydrocarbons with at least 10 carbon atoms which have been produced by Kolbe electrolysis of (a) at least one branched $C_6$-$C_{26}$ fatty acid or (b) a mixture of at least one linear $C_3$-$C_{26}$ fatty acid and at least one branched $C_4$-$C_{26}$ fatty acid as oil components with good spreading properties or as a silicone substitute in cosmetic compositions.

The present application also provides a method for the production of cosmetic and/or pharmaceutical compositions, wherein a hydrocarbon with at least 10 carbon atoms, which is obtained by Kolbe electrolysis of (a) at least one branched $C_6$-$C_{26}$ fatty acid or (b) a mixture of at least one linear $C_3$-$C_{26}$ fatty acid and at least one branched $C_4$-$C_{25}$ fatty acid, as the oil phase, which optionally contains additional oil-soluble components, is processed together with an aqueous phase, which optionally contains additional water-soluble components, and optionally, further auxiliary substances and additives to yield an emulsion. Kolbe electrolysis is preferably carried out on undiluted fatty acids or with fatty acids in a solvent, wherein 1-25 mol % of the fatty acids are neutralized with a base and electrolysis is carried out at current densities of 100-1000 mA/cm$^2$ and a temperature of 0-70° C.

Kolbe Electrolysis (General Method)

The fatty acids are used either pure or in a solvent (preferably: methanol; particularly preferably: methanol with water (to 1-5 wt. %, preferably 2.5-3 wt. %)). Some of the acid (1-25, preferably 5-15 mol %) is neutralized with a base (the preferred base is sodium methanolate). Electrolysis is carded out on electrodes made of platinum, platinum/niobium, or graphite or glassy carbon. The current density is 100-1000 mA/cm$^2$ (preferably 150-700 mA/cm$^2$, particularly preferably 200-600 mA/cm$^2$). Electrolysis is carried out at 0-70° C. (preferably 35-50° C.).

Since the resulting hydrocarbons are not miscible with the polar reaction solution (carboxylic acid in methanol), the products precipitate out in a second phase. This phase can be separated and contains the desired hydrocarbon (emollient) in high purity.

The hydrocarbons produced by Kolbe electrolysis exhibit better spreading properties than comparable hydrocarbons (see the FIGURE). For this purpose, a drop of 25 µl is dripped onto filter paper at 24° C. and 40% humidity. Automatic spreading of the drop is plotted against time on a diagram. The faster the drop spreads out, the better are the spreading properties.

Cosmetic/Pharmaceutical Preparations

Hydrocarbons produced by Kolbe electrolysis permit the production of stable cosmetic and pharmaceutical emulsions, optionally with spreading cascades (mixture of oils with different spreading rates), are also suitable as a silicone substitute in cosmetic and pharmaceutical compositions.

The compositions according to the invention can be formulations for body care, for example body milk, creams, lotions, sprayable emulsions, products for the elimination of the body odor etc. The hydrocarbons can also be used in surfactant-containing formulations as, for example, foam and shower baths, shampoos and hair conditioners. Depending on the intended application, the cosmetic formulations contain a series of auxiliary substances and additives, such as for example surfactants, additional oil components, emulsifiers, pearlescent wax, consistency agents, thickeners, super-fatting agents, stabilzers, polymers, fat, waxes, lecithins, phospholipids, biogenic active substances, UV absorbers, antioxidants, deodorants, antiperspirants, antidandruff agents, film-forming agents, swelling agents, insect repellents, tanning lotions, tyrosinase inhibitors (depigmentation agent), hydrotropes, solubilizers, preservatives, perfume oils, colorants etc., examples of which are listed below.

Surfactants

Anionic, nonionic, cationic and/or amphoteric or zwitterionic surfactants may be present as surface-active agents. In surfactant-containing cosmetic preparations, such as for example shower gels, foam baths, shampoos etc., the presence of at least one anionic surfactant is preferred. The proportion of surfactants is here conventionally from approx. 1 to 30, preferably 5 to 25 and in particular 10 to 20 wt. %.

Typical examples of anionic surfactants are soaps, alkyl benzene sulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and the salts thereof, fatty acid isethionates, fatty acid sarcosinates, fatty acid taurides, N-acylamino acids, such as for example acyl lactylates, acyl tartrates, acyl glutamates and acyl aspartates, alkyl oligoglucoside sulfates, protein fatty acid condensation products (in particular wheat-based vegetable products) and alkyl (ether) phosphates. If the anionic surfactants contain polyglycol ether chains, they may exhibit a conventional but preferably narrowed, distribution of homologues.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolyzates (in particular wheat-based vegetable products), polyol fatty acid esters, sugar esters, sorbitan esters, polysorbates and amine oxides. If the nonionic surfactants contain polyglycol ether chains they may exhibit a conventional, but preferably narrowed, distribution of homologues.

Typical examples of cationic surfactants are quaternary ammonium compounds, such as for example dimethyl distearyl ammonium chloride, and ester quats, in particular quaternized fatty acid trialkanolamine ester salts.

Typical examples of amphoteric or zwitterionic surfactants are alkyl betaines, alkylamido betaines, aminopropionates, aminoglycinates and imidazolinium betaines and sulfo-betaines.

The stated surfactants are exclusively known compounds. Reference is made to relevant review articles in this field with regard to the structure and production of these compounds. Typical examples of especially mild, i.e. especially skin-friendly surfactants, are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamido betaines, amphoacetals and/or protein fatty acid condensation products, the latter preferably based on wheat proteins.

Oil Components

Body care products such as creams, lotions and milks usually contain a series of oil components and emollients, which contribute to the further optimization of sensory properties. The oil components are usually present a total quantity of 1-50 wt. %, preferably 5-25 wt. % and in particular 5-15 wt. %.

Further examples of oil components are Guerbet alcohols based on fatty alcohols with 6 to 18, preferably 8 to 10 carbon atoms, ester of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols such as, for example, myristyl myrstate, myristyl isostearate, myristyl palmitate, myristyl stearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl stearate, isostearyl myrstate, isostearyl palmitate, isostearyl behenate, isostearyl oleate, isostearyl isostearate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate.

Also suitable are esters of linear $C_6$-$C_{22}$ fatty acids with branched alcohols, in particular 2-ethylhexanol, esters of $C_{18}$-$C_{38}$ alkylhydroxycarboxylic acids with linear or branched $C_6$-$C_{22}$ fatty alcohols, in particular dioctyl malate, esters of linear and/or branched fatty acids with polyhydric alcohols (such as for example propylene glycol, dimer diol or trimer triol) and/or Guerbet alcohols. Triglycerides based on $C_6$-$C_{10}$ fatty acids, liquid mono-/di/-/triglyceride mixtures based on $C_6$-$C_{18}$ fatty acids. Esters of $C_6$-$C_{22}$ fatty alcohols and/or Guerbet alcohols with aromatic carboxylic acids, in particular benzoic acid, esters of $C_2$-$C_{12}$ dicarboxylic acids with linear or branched alcohols with 1 to 22 carbon atoms or polyols with 2 to 10 carbon atoms and 2 to 6 hydroxyl groups. Vegetable oils, branched primary alcohols, substituted cyclohexanes, linear and branched $C_6$-$C_{22}$ fatty alcohol carbonates such as for example dicaprylyl carbonates (Cetiol® CC), Guerbet carbonates based on fatty alcohols with 6 to 18, preferably 8 to 10 C atoms, esters of benzoic acid with linear and/or branched $C_6$-$C_{22}$ alcohols (for example Finsolv® TN), linear or branched, symmetrical or asymmetrical dialkyl ethers with 6 to 22 carbon atoms per alkyl group, such as for example dicaprylyl ether (Cetiol® OE), ring-opening products of epoxidized fatty acids with polyols.

Fats and Waxes

Fats and waxes are added to body care products as care ingredients and are also used to improve the consistency of cosmetics. Typical examples of fats are glycerides, i.e. solid vegetable or animal products that substantially consist of mixed glycerol esters of higher fatty acids. In addition, fatty acid partial glycerides, i.e. technical mono- and/or diesters of glycerol with fatty acids with 12 to 18 carbon atoms such as glycerol mono-/dilaurate, -palmitate or -stearate. Waxes which may be considered are inter alia natural waxes such as candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin (wool grease), tail fat, ceresin, ozokerite (earth wax), petroleum jelly, paraffin waxes, microcrystalline waxes, chemically modified waxes (hard waxes), such as for example montan ester waxes, Sasol waxes, hydrogenated jojoba waxes as well as synthetic waxes such as polyalkylene waxes and polyethylene glycol waxes.

Apart from the aforementioned fats, the following fat-like substances, such as lecithins and phospholipids, may be considered as additives. Examples of natural lecithins which may be mentioned are cephalins, which are also known as phosphatidic acids and are derivatives of 1,2-diacyl sn-glycerol-3-phosphoric acids. In contrast, phospholipids are usually considered to be mono- and preferably diesters of phosphoric acid with glycerol (glycerol phosphates), which can generally be classified as fats. Sphingosines or sphingolipids may furthermore be considered.

Suitable thickeners are, for example, grades of Aerosil (hydrophilic silicas), polysaccharides, in particular xanthan gum, guar gum, agar-agar, alginates and tyloses, carboxymethylcellulose and hydroxyethyl- and hydroxypropylcellulose, polyvinyl alcohol, polyvinylpyrrolidone and bentonites, such as, for example, Bentone® gel VS-5PC (Rheox).

UV absorbers may be taken to be organic substances (light protection filters) which are liquid or crystalline at room temperature and are capable of absorbing ultraviolet radiation and then releasing the absorbed energy again in the form of longer wavelength radiation, for example heat. UV-B filters can be either oil-soluble or water-soluble. Derivatives of benzoylmethane may in particular be considered as typical UV-A filters. The UV-A and UV-B filters can, of course, be used in mixtures, for example, combinations of the derivatives of benzoylmethane, for example, 4-tert-butyl 4'-methoxydibenzoylmethane (Parsol® 1789) and 2-cyano-3,3-phenylcinnamic acid 2-ethylhexyl ester (octocrylene) as well as cinnamic acid esters, preferably 4-methoxycinnamic acid 2-ethylhexyl ester and/or 4-methoxycinnamic acid propyl ester and/or 4-methoxycinnamic acid isoamyl ester. Such combinations are often combined with water-soluble filters, such as 2-phenylbenzimidazole-5-sulfonic acid and the alkali metal, alkaline earth metal, ammonium, alkylammonium, alkanolammonium and glucammonium salts thereof.

In addition to the stated soluble substances, insoluble light-absorbing pigments, namely finely dispersed metal oxides may also be taken into consideration. Examples of suitable metal oxides are, in particular, zinc oxide and titanium dioxide. Apart from the two previously mentioned groups of primary light-absorbing substances, it is also possible to use secondary light-absorbing substances of the antioxidant type which interrupt the photochemical reaction chain which is initiated when ultra-violet radiation penetrates into the skin.

Biogenic active substances should be taken to mean, for example, tocopherol, tocopherol acetate, tocopherol palmitate, ascorbic acid, deoxyribonucleic acid and the fragmentation products thereof, β-lucans, retinol, bisabolol, allantoin, phytantriol, panthenol, AHA acids, amino acids, ceramides, pseudoceramides, essential oils, plant extracts such as for example prunus extract, bambara nut extract and vitamin complexes.

Deodorizing active substances counteract body odor, by either suppressing or eliminating them. Body odors arise through the action of skin bacteria on apocrine perspiration, wherein unpleasantly smelling degradation products are formed. Suitable deodorizing active substances are consequently microbial inhibitors, enzyme inhibitors, odor absorbers or odor suppressors.

Insect repellents which may, for example, be considered are N,N-diethyl-m-toluamide, 1,2-pentanediol or 3-(N-n-butyl-N-acetylamino)propionic acid ethyl ester, which is marketed by Merck KGaA under the name Insect Repellent® 3535, as well as butyl acetyl amino propionates.

Dihydroxyacetone is suitable as a self-tanning agent Tyrosine inhibitors, which prevent the formation of melanin and are used in depigmentation compositions, and may be considered are arbutin, ferulic acid, kojic acid, coumarinic acid and ascorbic acid (vitamin C).

Suitable preservatives are phenoxyethanol, formaldehyde solution, parabens, pentanediol or sorbic acid as well as the silver complexes known by the name Surfacine®, in addition to those substances listed in annex 6, parts A and B of the German regulations on cosmetics.

Mixtures of natural and synthetic odorous substances may be mentioned as perfume oils. Natural odorous substances are extracts from blossoms, stalks and leaves, fruit, fruit skins, roots, woods, herbs and grasses, needles and twigs, resins and balms. Animal raw materials, such as for example civet and castoreum, as well as combinations of the ester, ether, aldehyde, ketone, alcohol and hydrocarbon type may furthermore be taken into consideration.

Pearlescent waxes which may for example be considered, in particular for use in surfactant formulations, are: alkylene glycol esters, specifically ethylene glycol distearate; fatty acid alkanolamides, specifically coconut fatty acid diethanolamide; partial glycerides, in particular stearic acid monoglyceride; esters of polybasic, optionally hydroxy-substituted carboxylic acids with fatty alcohols with 6 to 22 carbon atoms, specifically long-chain esters of tartaric acid; fatty substances, such as for example, fatty alcohols, fatty ketones, fatty aldehydes, fatty ethers and fatty carbonates comprising in total at least 24 carbon atoms, in particular laurone and distearyl ether; fatty acids such as stearic acid, hydroxystearic acid or behenic acid, ring-opening products of olefin epoxides with 12 to 22 carbon atoms and fatty alcohols with 12 to 22 carbon atoms and/or polyols with 2 to 15 carbon atoms and 2 to 10 hydroxyl groups as well as the mixtures thereof.

Substances such as, for example, lanolin and lecithin as well as polyethoxylated or acylated lanolin and lecithin derivatives, polyol fatty acid esters, monoglycerides and fatty acid alkanolamides can be used as super-fatting substances, the latter simultaneously serving as foam stabilizers.

Metal salts of fatty acids, for example magnesium, aluminum and/or zinc stearate and/or ricinoleate can be used as stabilizers.

Hydrotropes, such as for example ethanol, isopropyl alcohol or polyols can furthermore be used to improve flow behavior. Polyols, which may be considered for this purpose, preferably contain 2 to 15 carbon atoms and at least 2 hydroxyl groups. The polyols can additionally contain further functional groups, in particular amino groups, or be modified with nitrogen.

EXAMPLES

Example 1

Electrolysis was carried out in an undivided 200 ml beaker cell. Two platinum sheet electrodes with a surface area of 1 cm² per electrode were positioned such that the distance between the electrodes was 1-3 mm. The electrodes were connected to a power supply (3 A/30 V). 40 g (0.28 mol) of ethylhexanoic acid, 2.5 g of sodium methanolate (0.014 mol. 30% in methanol) and 4.2 g of water were placed in the beaker cell and made up to 150 ml with methanol. The solution was electrolyzed with a constant current of 0.5 A while being stirred, a voltage of 26 V being required for this purpose. The cell was cooled with ice/water, such that a temperature of 40° C. was established. After 15 hours, electrolysis was terminated. A colorless product was produced as a second phase. Yield amounts to 16.0 g. Gas chromatographic investigation of the product revealed a diethyldecane content of >95% (see scheme).

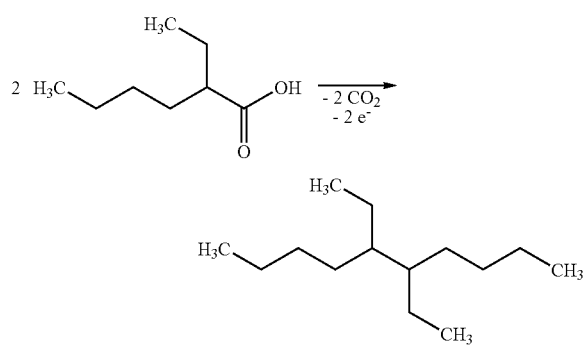

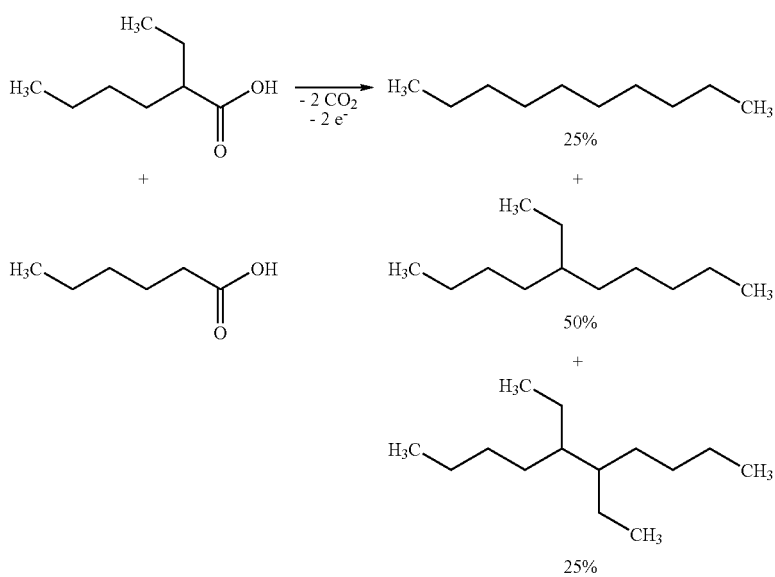

Example 2

Electrolysis was carried out in an undivided 200 ml beaker cell. Two platinum sheet electrodes with a surface area of 1 cm² per electrode were positioned such that the distance between the electrodes was 1-3 mm. The electrodes were connected to a power supply (3 A/30 V). 40 g (0.28 mol) of Cekanoic C8 (from Exxon), 2.5 g of sodium methanolate (0.014 mol, 30% in methanol) and 4.2 g of water were placed in the beaker cell and made up to 150 ml with methanol. The solution was electrolyzed with a constant current of 0.5 A while being stirred, a voltage of 26 V being required for this purpose. The cell was cooled with ice/water, such that a temperature of 40° C. was established. After 15 hours, electrolysis was terminated. A colorless product was produced as a second phase. Gas chromatographic investigation of the product revealed a content of >95% of branched C14 hydrocarbon comprising several isomers with methyl branches. These methyl branches have the same distribution pattern as the starting material Cekanoic C8. Yield amounts to 17.0 g.

Example 3

Electrolysis was carded out in an undivided 200 ml beaker cell. Two platinum sheet electrodes with a surface area of 1 cm² per electrode were positioned such that the distance between the electrodes was 1-3 mm. The electrodes were connected to a power supply (3 A/30 V). 23 g (0.16 mol) of ethylhexanoic acid, 18.5 g (0.16 mol) of hexanoic acid, 2.9 g of sodium methanolate (0.016 mol, 30% in methanol) and 4.2 g of water were placed in the beaker cell and made up to 150 ml with methanol. The solution was electrolyzed with a constant current of 0.4 A while being stirred, a voltage of 26 V being required for this purpose. The cell was cooled with ice/water such that a temperature of 40° C. was established. After 15 hours, electrolysis was terminated. A colorless product was produced as a second phase. Yield amounts to 18.5 g. Gas chromatographic investigation of the product revealed a mixture of three different hydrocarbons with a total content >95%. The three hydrocarbon substances are decane, ethyldecane and diethyldecane (see scheme)

The yields mentioned in the Examples are not optimized and can be further improved by routine optimization by a person skilled in the art.

| Cosmetic compositions All quantities stated in wt. % relative to the weight of the cosmetic preparation. | | |
|---|---|---|
| Commercial name | | wt. % |
| | INCI* name | |
| Emulgade PL68/50 | Cetearyl Glucoside (and) Cetearyl Alcohol | 5.00 |
| K Amphisol | Potassium Cetyl Phosphates | 0.50 |
| Cutine GMS-V | Glycerol Stearate | 1.00 |
| Diethyldecane | — | 6.00 |
| Myritol 318 | Caprylic/Capric Triglyceride | 5.00 |
| Novata AB | Cocoglycerides | 1.00 |
| Wacker silicone oil AK350 | Dimethicone | 0.30 |
| Carbopol | Carbomer | 0.30 |
| Glycerol, 99% | Glycerine | 5.00 |
| KOH (20%) | | 0.60 |
| Formaldehyde solution, 37.5% | | 0.15 |

-continued

Cosmetic compositions
All quantities stated in wt. % relative to the weight of the cosmetic preparation.

| Commercial name | | wt. % |
|---|---|---|
| H₂O distilled | | to make up to 100 |
| Viscosity [mPa · s]*) | | 12 5000 |
| | INCI* nomenclature | |
| Cutina GMS-SE | Glyceryl Stearate | 5.50 |
| Emulgin B1 | Ceteareth-12 | 0.20 |
| Cutina FS45 | Stearic Acid (and) Palmitic Acid | 2.00 |
| Lanette 16 | Cetyl alcohol | 1.50 |
| Fitoderm | Squalane | 6.00 |
| Diethyldecane | — | 5.00 |
| Cegesoft SH | *Shorea stenoptera* | 5.00 |
| Cegesoft PFO | *Passiflora incarnata* | 1.00 |
| Cetiol MM | Myristyl myristate | 1.00 |
| Glycerol, 99% | Glycerine | 5.00 |
| Formaldehyde solution, 37.5% | | 0.15 |
| H₂O distilled | | 93.85 |
| Viscosity [mPa · s]*) | | 18 7500 |

*International nomenclature for cosmetic Ingredients
*)Determined with TE spindle at 4 rpm, + Helipath at 23° C.

The invention claimed is:

1. A method for the production of cosmetic and/or pharmaceutical compositions comprising the steps of:
    (a) forming at least one hydrocarbon with at least 10 carbon atoms by performing Kolbe electrolysis of one or more fatty acids comprising at least one of pivalic acid and cyclohexanecarboxylic acid in combination with an acid that is selected from the group consisting of ethylhexanoic acid, isononanoic acid, isodecanoic acid, isostearic acid, unsaturated, branched $C_6$-$C_{26}$ monomer fatty acids, and neodecanoic acid, and mixtures thereof, wherein said Kolbe electrolysis comprises:
        (1) electrolyzing said one or more fatty acids to produce radicals that retain the structural characteristics of said fatty acids; and
        (2) dimerizing said radicals to form said hydrocarbon with at least 10 carbon atoms;
    wherein said hydrocarbon with at least 10 carbon atoms is characterized in that it contains components that retain the structural characteristics of said one or more fatty acids;
    (b) providing an aqueous phase; and
    (c) forming an emulsion by combining an oil phase comprising said at least one hydrocarbon with said aqueous phase.

2. The method as claimed in claim 1, wherein, the Kolbe electrolysis is carried out with undiluted fatty acids or with fatty acids dissolved in a solvent, wherein 1-25 mol % of the fatty acids are neutralized with a base and electrolysis is carried out at current densities of 100-1000 mA/cm² and a temperature of 0-70° C.

3. The method of claim 1 wherein said at least one hydrocarbon has no more than 22 carbon atoms.

4. The method of claim 1 wherein said at least one branched C6-C26 fatty acid exhibits no branching in the alpha position.

5. The method of claim 1 wherein said at least one hydrocarbon is a saturated hydrocarbon.

6. The method of claim 1, wherein said at least one hydrocarbon is present in a quantity of 0.1-50 wt. % relative to the total composition.

* * * * *